United States Patent
Takada et al.

(10) Patent No.: US 6,437,327 B2
(45) Date of Patent: *Aug. 20, 2002

(54) MASS SPECTROMETRY OF SOLUTION AND APPARATUS THEREFOR

(75) Inventors: Yasuaki Takada, Kokubunji; Minoru Sakairi, Tokorozawa; Atsumu Hirabayashi, Hachiouji; Takayuki Nabeshima, Kokubunji; Hideaki Koizumi, Setagaya-ku, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/859,508

(22) Filed: May 18, 2001

Related U.S. Application Data (63) Continuation of application No. 09/492,352, filed on Jan. 27, 2000, now Pat. No. 6,252,225, which is a continuation of application No. 08/968,898, filed on Nov. 6, 1997, now Pat. No. 6,121,608, which is a continuation of application No. 08/562,369, filed on Nov. 22, 1995, now abandoned.

(30) Foreign Application Priority Data

Nov. 28, 1994 (JP) .............................................. 6-292589

(51) Int. Cl.$^7$ ............................................... H01J 49/10
(52) U.S. Cl. ..................................................... 250/288
(58) Field of Search .................................. 250/288, 281, 250/282, 423 R (56) References Cited

U.S. PATENT DOCUMENTS

| | | |
|---|---|---|
| 4,209,696 A | 6/1980 | Fite |
| 4,546,253 A | 10/1985 | Tsuchiya et al. |
| 4,647,772 A | 3/1987 | Lewis et al. |
| 4,902,891 A | 2/1990 | Vestal |
| 4,960,991 A | 10/1990 | Goodley et al. |
| 4,960,992 A | 10/1990 | Vestal et al. |
| 5,015,845 A | 5/1991 | Allen et al. |

(List continued on next page.)

FOREIGN PATENT DOCUMENTS

| | | |
|---|---|---|
| JP | 60-079656 | 5/1985 |
| JP | 5-325882 | 12/1993 |
| JP | 61-02246 | 4/1994 |
| JP | 6-102246 | 4/1994 |

OTHER PUBLICATIONS

"Characteristics of a Liquid Chromatograph/Atmospheric Pressure Ionization Mass Spectrometer", M. Sakairi et al, pp. 774–780, 1988.

"A Mass Spectrometric Study of Positive and Negative Ion Formation in an $SF_6$ Corona. Part I: Sources of Sulphur–Fluoride Ions", I. Sauers et al, 1261, Journal of Physics D: Applied Physics 25, May 14, 1992, No. 5, Bristol, GA, pp. 761–773.

"Atmospheric–Pressure–Ionization Mass Spectrometry II. Applications in Pharmacy, Biochemistry and General Chemistry", A. P. Bruins, 8196 Trac: Trends in Analytical Chemistry, Feb. 13, 1994, No. 2, Amsterdam, NL pp. 81–90.

*Primary Examiner*—Kiet T. Nguyen
(74) *Attorney, Agent, or Firm*—Antonelli, Terry, Stout & Kraus, LLP (57) ABSTRACT

A mass spectrometer including a sprayer for spraying a sample solution, a needle electrode for ionizing the sample contained in the sample solution, an aperture for introducing the ions of the sample into a lower pressure region having a pressure lower than the pressure of a region in which the needle electrode is disposed, and a mass spectrometric apparatus for analyzing the ions introduced from the aperture. A direction of a spray caused by the sprayer is almost perpendicular to or at an angle with respect to a center axis of the aperture, and a tip of the needle is disposed facing to an electrode having the aperture.

5 Claims, 8 Drawing Sheets

U.S. PATENT DOCUMENTS

| | | |
|---|---|---|
| 5,051,583 A | 9/1991 | Mimura et al. |
| 5,103,093 A | 4/1992 | Sakairi et al. |
| 5,170,052 A | 12/1992 | Kato |
| 5,170,053 A | 12/1992 | Hail et al. |
| 5,495,108 A | 2/1996 | Apffel, Jr. et al. |
| 5,581,081 A | 12/1996 | Kato et al. |
| 5,726,447 A | 3/1998 | Aisawa et al. |
| 5,730,741 A | 3/1998 | Bertsch et al. |
| 5,750,988 A | 5/1998 | Apffel et al. |
| 5,844,437 A | 12/1998 | Whitehouse et al. |
| 5,877,495 A | 3/1999 | Takada et al. |
| 6,252,225 B1 * | 6/2001 | Takada et al. .............. 250/288 |

* cited by examiner

MASS SPECTROMETRY OF SOLUTION AND APPARATUS THEREFOR

CROSS REFERENCE TO RELATED APPLICATION

This is a continuation of U.S. application Ser. No. 09/492,352, filed Jan. 27, 2000 now U.S. Pat. No. 6,252,225, which is a continuation of U.S. application Ser. No. 08/968,898, filed Nov. 6, 1997, U.S. Pat. No. 6,121,608, issued Sep. 19, 2000, which is a continuation of U.S. application Ser. No. 08/562,369, filed Nov. 22, 1995, now abandoned, the subject matter of which is incorporated by reference herein.

BACKGROUND OF THE INVENTION

The present invention relates to mass spectrometry of a solution, and particularly to a mass spectrometer for analyzing substances in a solution and an apparatus for combining a liquid chromatograph used for separation and analysis of a mixed sample and the mass spectrometer.

At present, development of mass spectrometry of biological substances is regarded as important in the field of analysis. Biological substances are generally dissolved in a solution as a mixture, so that an apparatus for combining a means for separating a mixture and a mass spectrometer is under development. As a typical apparatus of this method, there is a liquid chromatograph-mass spectrometer (hereinafter abbreviated to LC/MS) available. A liquid chromatograph (hereinafter abbreviated to LC) is superior in separation of a mixture but cannot identify each substance, whereas a mass spectrometer hereinafter abbreviated to MS) is highly sensitive and superior in identification ability but not suitable to analysis of a mixture. Therefore, an LC/MS using an MS as an LC detector is very useful in analysis of a mixture.

The LC/MS using the conventional atmospheric pressure chemical ionization method which is disclosed in Japanese Patent Application Laid-Open 5-325882 will be explained hereunder by referring to FIG. 9.

A sample solution eluted from a liquid chromatograph 14 is introduced into a metallic tube 3 via a pipe 1 and a connector 2. The sample solution comprises a sample and a mobile phase (a buffer solution which flows into the separation column when the sample is separated in the LC). However, for the purpose of improving the ionization efficiency in the ion source (according to the present invention, the term "ion source" means a portion for converting a substance to be analyzed existing in the liquid phase to ions in the gas phase and includes a spray portion for spraying a solution, a vaporization portion for vaporizing droplets generated by the spray portion, and an ionization portion for ionizing a substance), a solvent different from the mobile phase may be added. The metallic tube 3 is embedded in a metallic block 4a. When the metallic block 4a is heated by a heating means such as a heater, a sample solution introduced in the metallic tube 3 is sprayed. Fine droplets generated by spraying are introduced into and vaporized in a vaporization portion 5 comprising a heated metallic block 4b.

Sample molecules vaporized in the vaporization portion 5 are introduced into the ionization portion 6. A needle electrode 7 is installed in the ionization portion 6. When a high voltage is applied to this needle electrode 7 from a high voltage source 8a, a corona discharge is generated in the ionization portion 6.

Assuming A to be sample molecules to be analyzed and B to be molecules of a reaction gas, the atmospheric pressure chemical ionization method is a method for ionizing A by a chemical reaction of A and B. As a typical ion chemical reaction, there are a protonation reaction and a deprotonation reaction available as shown below.

$A + BH^{3O} \rightarrow AH^+ B$ (Protonation reaction)

$A + B^- \rightarrow (A-H)^- + BH$ (Deprotonation reaction)

Figure 9:
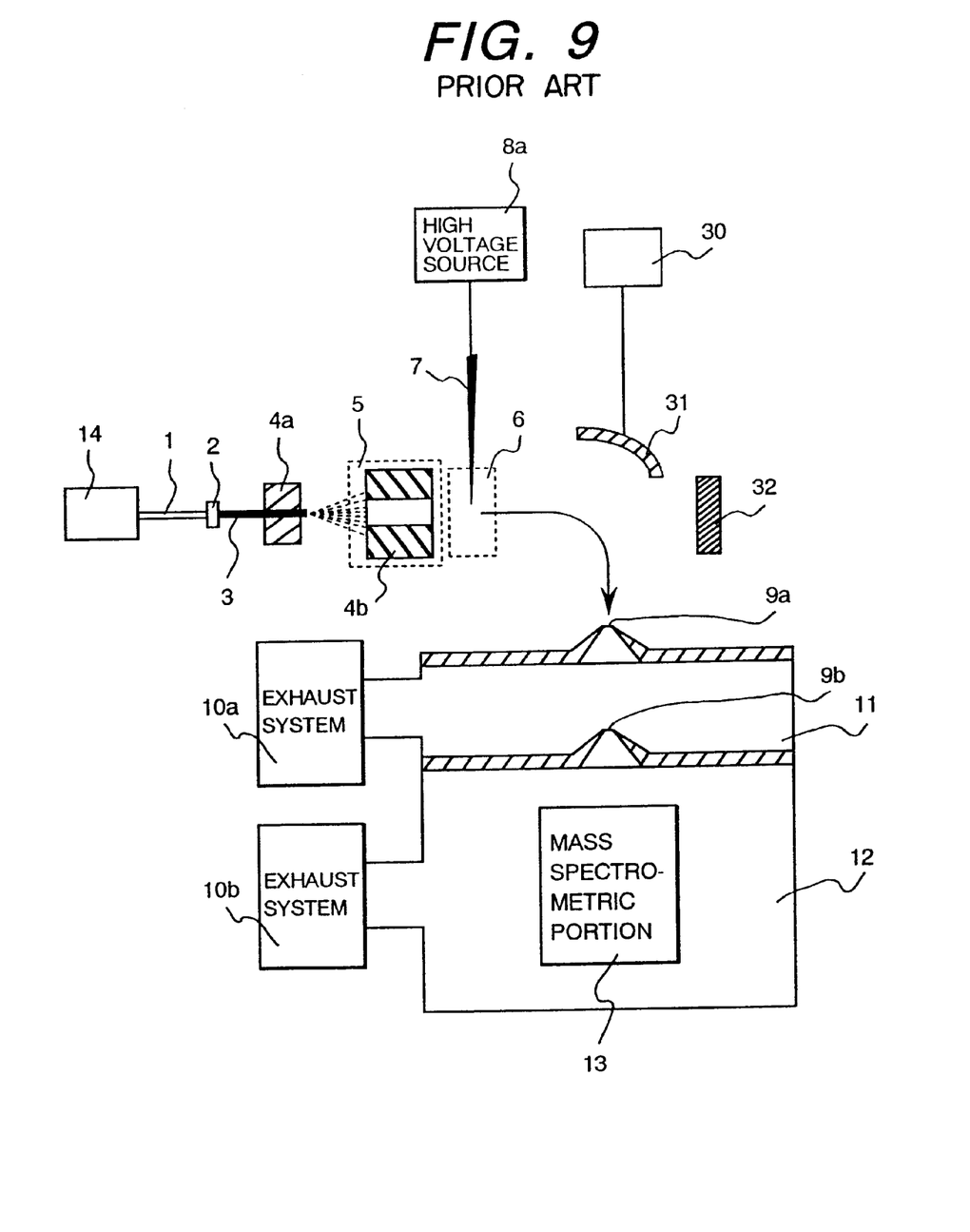
FIG. 9 is a schematic view showing the constitution of a liquid chromatograph-mass spectrometer using the conventional atmospheric pressure chemical ionization method.

According to the prior art shown in FIG. 9, hydronium ions ($H_3O^+$) are generated when a corona discharge is generated in the atmosphere and ions Ali+ of the sample A are generated by using the following reaction between the hydronium ions and the sample molecules A.

$A + H_3O^+ \rightarrow AH^+ + H_2O$

Ions of the sample generated by chemical ionization in the ionization portion 6 have their trajectory deflected by a voltage applied to a deflection electrode 31 by a power source 30 and drift toward an ion introduction aperture 9a. The ions pass through the ion introduction aperture 9a and are introduced into a high vacuum portion 12 which is exhausted to a high vacuum by an exhaust system 10b via a differential pumping portion 11 which is evacuated by an exhaust system 10a and an ion introduction aperture 9b. When ions and solvent molecules pass through the ion introduction apertures 9a and 9b, they are cooled by adiabatic expansion, so that so-called clustering for condensing the ions and solvent molecules again occurs. To prevent the clustering, electrodes in which the ion introduction apertures 9a and 9b are formed are heated. The mass of ions introduced into the high vacuum portion 12 is analyzed by a mass spectrometric portion 13. Nonvolatile compounds that are not ionized in the ionization portion 6 are diffused in the atmosphere and captured by a capture plate 32.

An LC/MS using the conventional electrospray method which is disclosed in Japanese Patent Application Laid-Open 6-102246 will be explained by referring to FIG. 10. A sample solution eluted from the LC is introduced into the metallic tube 3 via the pipe 1 and the connector 2. A high voltage is applied between the metallic tube 3 and an electrode 21c in which the ion introduction aperture 9a is formed by using a high voltage source 8b and the sample solution is electrostatically sprayed. To assist electrospray, gas such as nitrogen gas is let flow from a spray gas outlet 40. When fine charged droplets generated by electrospray are vaporized, gaseous ions are generated. However, the diameter of droplets at the center of the jet is large and it is difficult to vaporize droplets with a large diameter, and furthermore when droplets with a large diameter adhere to the electrode 21c, the temperature of the electrode 21c drops and the ion intensity obtained in the mass spectrometric portion may vary. Therefore, a shielding plate 41 for shielding the center of the jet is installed between the metallic tube 3 and the electrode 21c and the outer periphery of the jet is sprayed toward the ion introduction aperture 9a. Generated ions are introduced into the high vacuum portion 12 via the ion introduction aperture 9a, the differential pumping portion 11, and the ion introduction aperture 9b and analyzed by the mass spectrometric portion installed in the high vacuum portion 12.

For analysis of biological substances and environmental contaminants, a method for analyzing a sample solution containing nonvolatile compounds of high concentration is required.

For example, in the LC, the mobile phase including a nonvolatile salt is often used experientially so as to enhance the separation ability and the reproducibility of the retention time. As a result, a method for analyzing a sample solution containing a nonvolatile salt is desirable for a detector of the LC.

Nonvolatile compounds are contained not only in samples obtained from a living organism such as urine, perspiration, and blood, but also is samples relating to the environment such as effluents from a factory and water of a lake or marsh. To remove nonvolatile compounds from these samples, a complicated pretreatment such as desalting is required. Therefore, in order to analyze biological substances and environmental contaminants quickly, a method for analyzing a sample solution containing nonvolatile compounds is required.

However, in a mass spectrometric apparatus using the conventional atmospheric pressure chemical ionization method shown in FIG. 9, when a sample solution containing nonvolatile compounds of high concentration is introduced into the ion source of the mass spectrometric apparatus comprising an ion source, a differential pumping portion, and a mass spectrometric portion, a problem arises that ions of a substance to be analyzed cannot be analyzed stably for many hours. The reason is that since the sample solution is sprayed by using the heated metallic tube, solvent molecules are vaporized in the tube and nonvolatile compounds are salted out on the inner wall of the tube. The inner diameter of the metallic tube becomes smaller because nonvolatile compounds are salted out on the tube wall, and the metallic tube finally clogs up. Therefore, the spray status varies with time, so that the ion generation in the ionization portion is adversely affected.

When fine droplets containing nonvolatile compounds adhere to the neighborhood of the ion introduction aperture installed between the ion source and the differential pumping portion, solvent molecules are vaporized and nonvolatile compounds are salted out around the aperture. In the conventional apparatus shown in FIG. 9, by installing the capture plate on the ion source side, a method for salting out nonvolatile compounds contained in droplets adhered to the capture plate on the capture plate is used so as to reduce salting out of nonvolatile compounds around the aperture. However, it is actually difficult to capture all droplets sprayed in the atmosphere on the capture plate and some of the droplets are diffused in the atmosphere and reach the aperture. Therefore, if the analysis is continued for many hours, an actual problem arises that salted nonvolatile compounds clog up the aperture and ions cannot be introduced into the mass spectrometric portion.

As an example of a sample solution containing nonvolatile compounds, a case where a sodium phosphate water solution (hereinafter described as a phosphoric acid buffer) having a concentration of 20 millimoles/liter is introduced into the ion source at a flow rate of 50 microliters per minute will be described. A phosphoric acid buffer is a mobile phase which is often used in a detector other than the MS, for example, in an LC having an ultraviolet absorption detector. When a conventional LC/MS uses a phosphoric acid buffer, the observed ion intensity starts dropping within about 30 minutes after the start of analysis and drops down to about $\frac{1}{10}$ of the initial value after one hour has elapsed, and the continuation of analysis becomes difficult.

Whether a problem that the metallic tube or aperture clogs tip due to salting out of nonvolatile substances arises or not depends on the kind of nonvolatile substances and the total amount of nonvolatile substances (namely, the concentration of nonvolatile substances and the flow rate of the sample solution) introduced into the ion source. For example, when substances are analyzed at a flow rate of 1 microliter per minute continuously for several hours using a phosphoric acid buffer having a concentration of 10 millimoles/liter, the ion intensity observed by the mass spectrometer may decrease.

Figure 10:
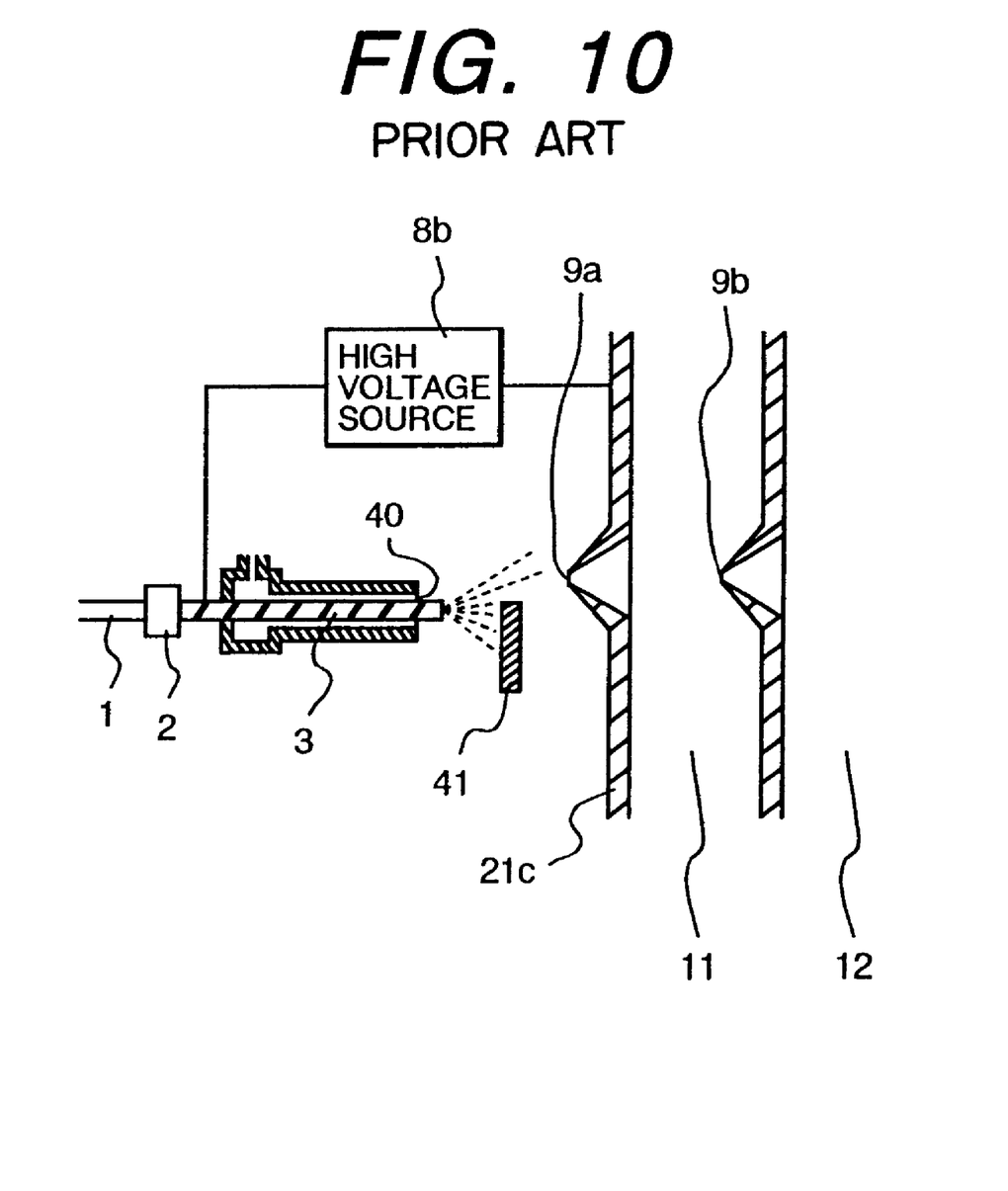
FIG. 10 is a schematic sectional view showing the constitution of a liquid chromatograph-mass spectrometer using the conventional electrospray method.

Even in the apparatus using the conventional electrospray method shown in FIG. 10, the outer periphery of a jet is sprayed toward the ion introduction aperture, so that some of the droplets generated by the spray reach the neighborhood of the ion introduction aperture. Therefore, when a sample solution containing nonvolatile compounds of high concentration is introduced into the ion source, there is a possibility that the ion introduction aperture may clog up with nonvolatile compounds salted out by vaporization of droplets. Therefore, in the same way as with an apparatus using the atmospheric pressure chemical ionization method shown in FIG. 9, a problem arises that if the analysis is continued for many hours, the aperture clogs up and ions cannot be introduced into the mass spectrometric portion.

For the aforementioned reason, an apparatus having an ion source allowing stable analysis for many hours even if a solution containing nonvolatile compounds of high concentration is introduced is required.

SUMMARY OF THE INVENTION

An object of the present invention is to prevent a metallic tube and an ion introduction aperture from clogging up by salting out of nonvolatile compounds. Another object of the present invention is to allow analysis by an LC/MS using a mobile phase containing a nonvolatile salt which cannot be used for many hours conventionally.

According to the present invention, the above objects are accomplished by introducing a sample solution containing nonvolatile compounds sent to the ion source into the metallic tube, spraying the sample solution by electrospray at a high voltage applied between the metallic tube and the electrode externally installed, ionizing gaseous sample molecules obtained by vaporizing obtained droplets by chemical reaction, and analyzing ions of sample molecules by the MS.

Namely, the present invention is characterized in the method and constitution that nonvolatile compounds contained in a sample solution are ionized by the first ionization means and removed by the electric field, and then a substance contained in the sample solution to be analyzed is ionized by the second ionization means, and ions of the target substance are analyzed by the spectrometric portion.

Since a sample solution sent to the ion source is sprayed by electrospray, no nonvolatile compounds will be salted out by vaporization of solvent molecules and the metallic tube can be prevented from clogging.

Electrospray is a method for collecting ions in a solution on the liquid surface by the electric field and crushing the solution by the force of repulsion acting between ions so as to generate fine charged droplets. When charged droplets obtained by electrospray are vaporized, ions existing in the solution can be fetched in the gas phase. Therefore, some of nonvolatile compounds which exist in the solution as ions can be converted to gaseous ions by electrospray. Ions generated by electrospray are drifted by the electric field between the metallic tube and the metallic block constituting the vaporization portion and captured by the metallic block or the trajectory thereof is curved by the potential applied to the needle electrode installed in the ionization portion, so that they cannot reach the ion introduction aperture. Therefore, no nonvolatile compounds will salt out around the ion introduction aperture and the aperture will not be clogged out.

A substance to be analyzed which is not ionized in the solution is not converted to gaseous ions by electrospray but diffused in the atmosphere as gaseous molecules which are electrically neutral and reaches the ionization portion. In the ionization portion, ions of the substance to be analyzed are generated by a corona discharge generated by the needle electrode and chemical ionization reaction caused by it. Ions of the substance to be analyzed are fetched and analyzed by the mass spectrometric portion in a vacuum via the ion introduction aperture.

A nonvolatile salt which is represented by sodium phosphate is dissociated in a solvent such as water and exists as ions. Therefore, the LC/MS of the present invention can use a mobile phase containing a nonvolatile salt which is represented by a phosphoric acid buffer though it is conventionally difficult to use for many hours.

DESCRIPTION OF THE PREFERRED EMBODIMENTS

Figure 1:
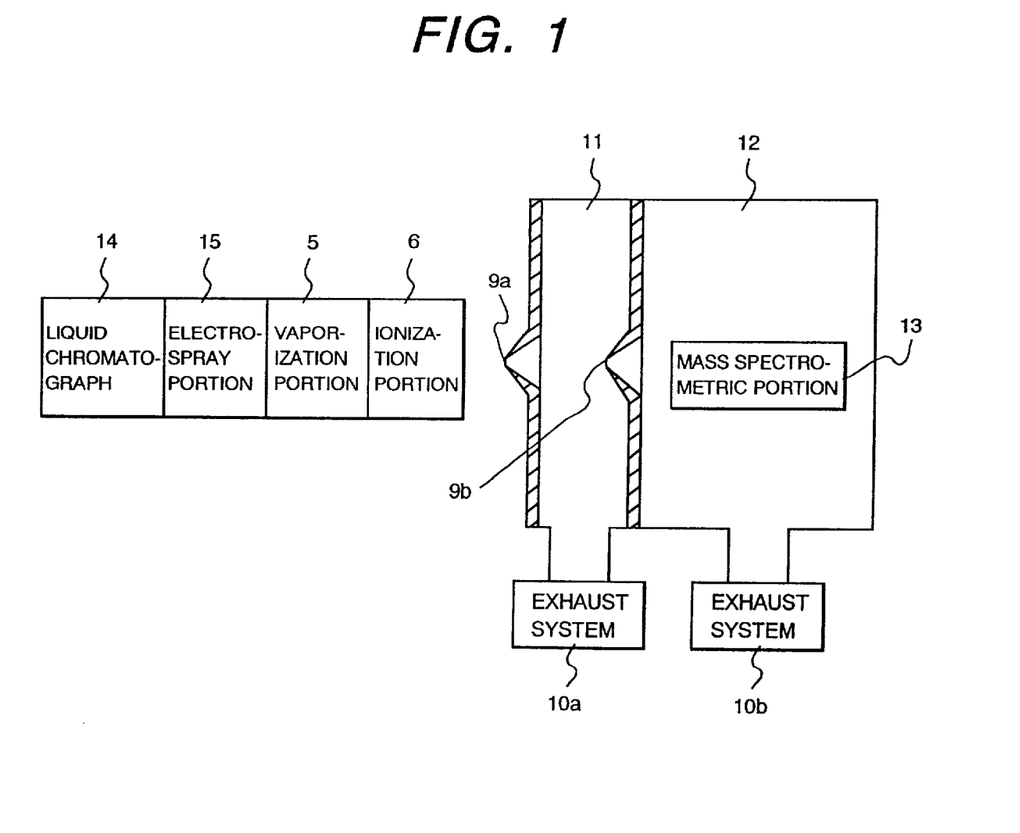
FIG. 1 is a schematic view showing the constitution of a mass spectrometric apparatus using an electrospray method as a first ionization means and a chemical ionization method as a second ionization means which is an embodiment of the present invention.

FIG. 1 is a schematic view showing the constitution of the mass spectrometric apparatus of the present invention. A sample separated by a liquid chromatograph 14 is sprayed by an electrospray portion 15 together with the mobile phase. The sample and the mobile phase constitute a sample solution including a solvent and a solute. Droplets obtained by spray are promoted in vaporization in a vaporization portion 5. Gaseous sample molecules generated by the ionization portion 5 are ionized by chemical reaction in an ionization portion 6. Ions of the sample generated by the ionization portion 6 are introduced into an ion introduction aperture 9b and a high vacuum portion 12 which is exhausted by an exhaust system 10b via an ion introduction aperture 9a and a differential pumping portion 11 which is exhausted by an exhaust system 10a.

Ions introduced into a vacuum are analyzed in mass by a mass spectrometric portion 13. The ionization portion 6 may be installed in the differential pumping portion 11. The differential pumping portion 11 has a pressure between several Pascal to several hundreds Pascal and can generate ions by chemical reaction because sample molecules and reaction gas collide with each other.

Figure 2:
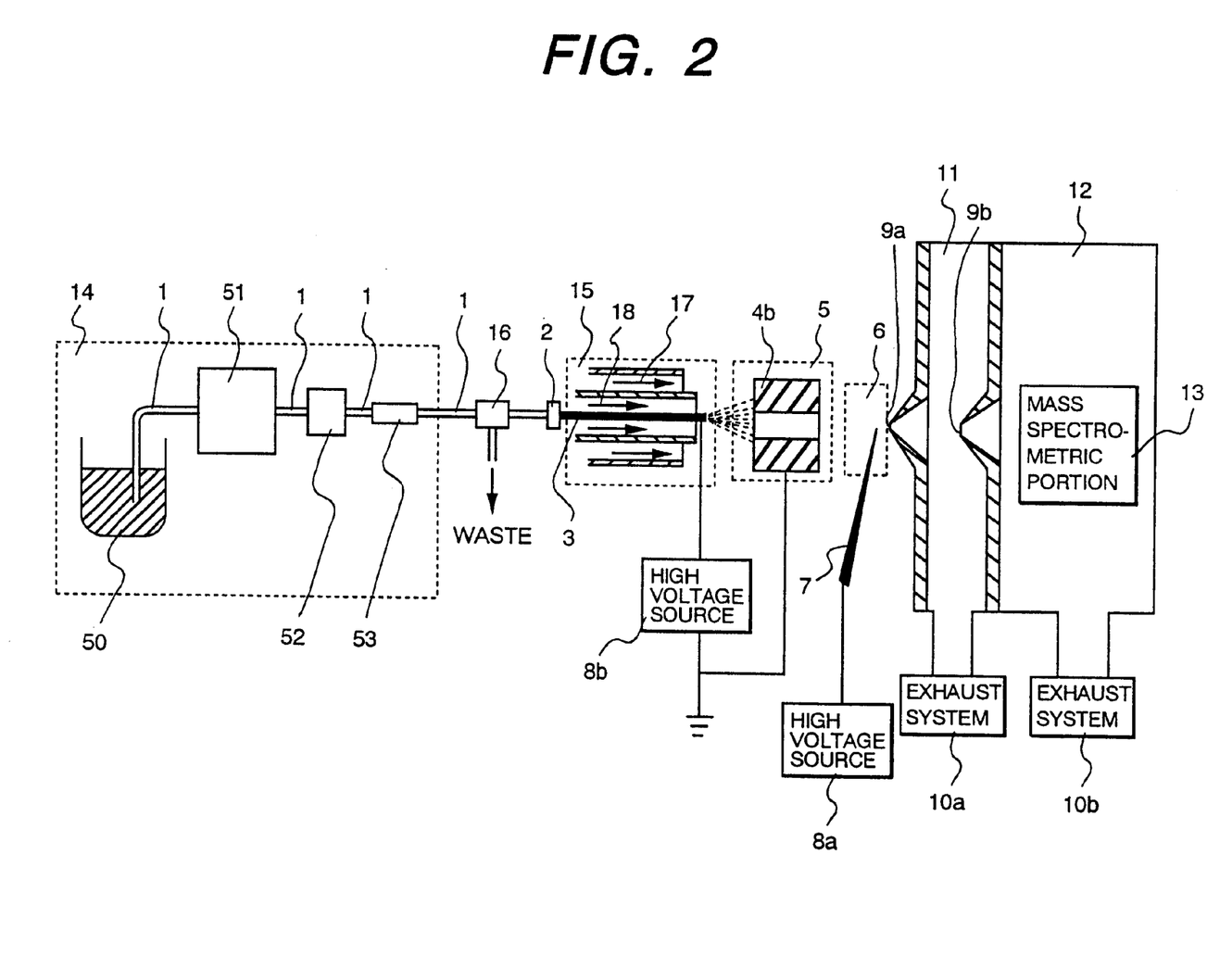
FIG. 2 is an illustration for explaining the embodiment shown in FIG. 1 in detail.

FIG. 2 is a drawing showing a more detailed structure than the constitution shown in FIG. 1. The liquid chromatograph 14 comprises a mobile phase reservoir 50, a pump 51, a sample introduction portion 52, a separation column 53, and a pipe 1. A mobile phase in the mobile phase reservoir 50 is pumped up by the pump 51 and sent to the sample introduction portion 52 and the separation column 53 at the predetermined flow rate via the pipe 1. The sample is introduced from the sample introduction portion 52 and sent to the separation column 53 together with the mobile phase. The separation column 53 is filled tip with a packing material. The sample is separated by interaction with the packing material. The sample solution eluted from the separation column 53 is introduced into the metallic tube 3 via the pipe 1 and the connector 2. When a high voltage is applied between the metallic tube 3 and the metallic block 4b by using a high voltage source 8b, charges with the same sign are accumulated on the surface of the solution by the electric field in the neighborhood of the end of the metallic tube 3. When the electrostatic repulsion force generated by the accumulated charges becomes stronger than the surface tension of the solution, so-called electrospray for generating many fine charged droplets is caused. Fine droplets generated by spray are introduced into the vaporization portion 5 comprising the heated metallic block 4b. The metallic block 4b is heated at about 300° C. by a heater (not shown in the drawing). Droplets generated by spray are vaporized by heat while they are passing through the aperture of the metallic block 4b.

Sample molecules vaporized in the vaporization portion 5 are introduced into the ionization portion 6. The needle electrode 7 is installed in the ionization portion 6. When a high voltage is applied to this needle electrode 7 by using the high voltage source 8a, a corona discharge is generated in the ionization portion 6. When gaseous sample molecules obtained by volatilization of droplets reach the corona discharge portion, a chemical reaction with primary ions such as hydronium ions generated by the corona discharge is caused and ionization of sample molecules is realized.

In this case, since the sample solution is sprayed by electrospray, nonvolatile compounds will not be salted out by vaporization of solvent molecules and the metallic tube 3 can be prevented from clogging up. The part of the nonvolatile compounds in the solution which is ionized is converted to gaseous ions by electrospray. These ions are captured by the metallic block 4b constituting the vaporization portion 5 or the trajectory thereof is curved by the potential applied to the needle electrode 7 installed in the ionization portion 6, so that they cannot reach the ion introduction aperture 9a. Therefore, even if a sample solution containing nonvolatile compounds is used, the nonvolatile compounds will not salt out around the ion introduction aperture 9a and there is no possibility that the ion introduction aperture 9a is clogged up.

Therefore, according to the present invention, even if a sample solution containing nonvolatile compounds of high concentration is introduced, an ion source for generating ions of a substance to be analyzed stably for many hours can be realized. Furthermore, according to the present invention, a mass spectrometric apparatus for analyzing a sample solution containing nonvolatile compounds of high concentration stably for many hours can be realized.

The polarity (positive or negative) of voltages to be applied to the needle electrode 7 and the metallic tube 3 by the high voltage sources 8a and 8b may be switched independently of each other according to the property of a substance to be analyzed and the property of nonvolatile compounds in the sample solution. For example, when a substance to be analyzed has a strong proton affinity and is apt to be converted to protonated ions, it is desirable to apply a positive voltage to the needle electrode 7. When a substance to be analyzed has a property that negative ions which are deprotonated are easily generated, it is desirable to apply a negative voltage to the needle electrode 7.

Next, the effect of the present invention described in FIG. 2 will be explained on the basis of the experimental results. A 50% methanol water solution containing sodium dihydrogenphosphate having a concentration of 20 millimol/liter is used as a mobile phase and fed to the ion source by an LC pump at a flow rate of 50 micro liter per minute. β-hydroxytheophylline (concentration 100 ppm) is used as a sample. This sample is introduced from an LC sample injector in units of 2 micro liters each time by taking time. The mass spectrometer monitors protonated molecular ions (molecular weight 225) of β-hydroxytheophylline.

Figure 11:
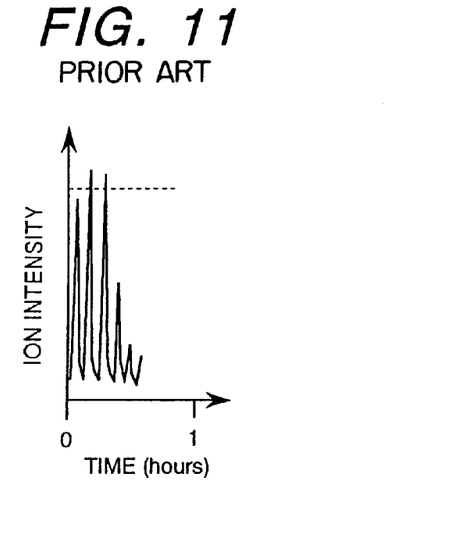
FIG. 11 is a graph showing a change with time of the ion intensity obtained by a mass spectrometer using the conventional atmospheric pressure chemical ionization method.

FIG. 11 shows a change with time of the ion intensity observed by an apparatus using the conventional atmospheric pressure chemical ionization method. The ion intensity starts reduction about 30 minutes after start of analysis. When the apparatus is disassembled and examined, it is found that the cause of reduction of the ion intensity is that a nonvolatile salt (sodium phosphate) in the mobile phase salts out in the neighborhood of the ion introduction aperture and the ion introduction aperture is clogged up.

Figure 12:
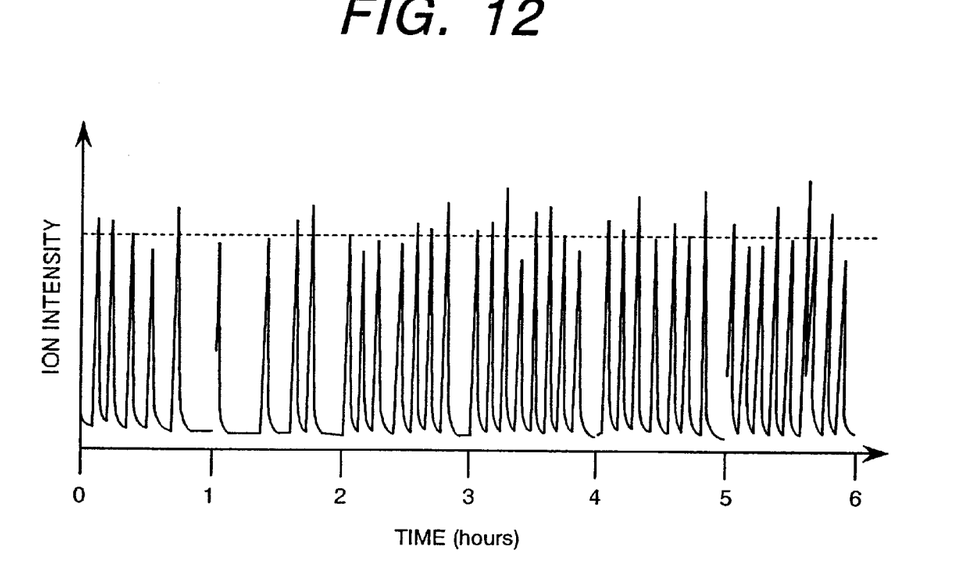
FIG. 12 is a graph showing a change with time of the ion intensity obtained by the mass spectrometer of the present invention.

FIG. 12 shows a change with time of the ion intensity measured by using the apparatus of the present invention shown in FIG. 2. The dotted line shown in the drawing indicates the mean level of the maximum values of the ion intensity when each sample is introduced and almost the same intensity is obtained over a period of 6 hours. As shown in FIG. 12, according to the present invention, even if a mobile phase containing a nonvolatile salt is introduced into the ion source, a reduction in the ion intensity caused by clogging of the metallic tube or ion introduction aperture is not seen and ions are observed stably for many hours.

As shown in FIG. 11, if a mobile phase containing a nonvolatile salt is used in the conventional LC/MS under the aforementioned condition, a cleaning operation for the aperture and others is required every analysis for about 30 minutes. To clean the aperture, it is necessary to stop the exhaust system aha disassemble the apparatus. To restart analysis, it requires about 2 hours including the time of reexhaust after completion of cleaning, so that the operability as an analytical apparatus is extremely bad. Furthermore, when the vacuum pump starts exhausting from the atmospheric pressure to a vacuum, it is applied with a great load, so that repetition of stopping and reexhausting the exhaust system is a factor for shortening the life time of the vacuum pump. Furthermore, when the apparatus is disassembled and assembled again, the analytical conditions are changed by a shift in installation position of each part constituting the ion source and a change in temperature of the heating part, and the reproducibility of the ion intensity observed by the mass spectrometer is bad, and the accuracy of quantitative analysis of a substance to be analyzed gets worse. In the conventional apparatus, it is necessary to end one analysis including adjustment of the ion source for 30 minutes during which ions are observed stably. However, a time of 30 minutes is not always sufficient for use of the separation ability of the LC at its maximum. For example, there is a method available for changing the composition of a mobile phase with time and eluting a substance to be analyzed. However, if the composition is changed in a short time, no sufficient separation may be obtained. The cause thereof is considered to be that if the composition of the mobile phase is changed too fast, the packing material in the separation column and the mobile phase cannot be kept in the equilibrium state.

The apparatus of the present invention can be used continuously for about 10 hours even if a mobile phase containing a nonvolatile salt which is conventionally difficult to use is used. If an operator cleans and adjusts the apparatus before starting operation every morning, he can obtain data during his operation in a day. Therefore, the apparatus of the present invention has advantages that the operability is remarkably improved compared with a conventional apparatus, and the burden imposed on the vacuum pump is lightened, and the life time of the vacuum pump can be lengthened. The apparatus of the present invention is characterized in that since it can repeat measurement under the same analytical condition, the accuracy of quantitative analysis is high and a sufficient time can be put in separation, so that analysis by the LC/MS fully utilizing the separation ability of the LC is possible.

Whether a problem that ions cannot be observed stably due to clogging of the metallic tube or aperture arises or not depends on the kind of nonvolatile substances and the total amount (namely, the concentration of nonvolatile substances and the flow rate of the solution) sent to the ion source.

For example, there is a capillary electrophoresis method (hereinafter abbreviated to CE) available as a separation means different from the LC. This is a method for separating a sample by electrophoresis using a fused-silica capillary of several tens microns in inner diameter. A buffer solution containing a nonvolatile salt having a concentration of several tens millimol/liter may be used as a separation medium of CE. A flow of a buffer solution which is called an electro-osmosis flow is generated due to dissociation of the inner wall of the capillary, though the rate of electro-osmosis flow is generally low such as 0.1 micro liter per minute or less. Therefore, in a so-called CE/MS using an MS as a CE detector, a problem of clogging of the aperture will not arise.

When the flow rate of a solution sent from the LC is high and it is difficult to continue electrospray stably, as shown in FIG. 2, a splitter 16 may be installed so as to introduce a part of the solution into the metallic tube 3. Also as shown in FIG. 2, a spray gas 17 may flow from the outside of the metallic tube 3 so as to assist the electrospray.

When a narrow separation column with an inner diameter of from several lens microns to several hundreds microns which is called a capillary column is used in the LC, it may be difficult to continue the electrospray stably because the flow rate of a solution sent from the LC is low. It may be also difficult to continue the electrospray stably because the viscosity or electric conductivity of the solution is excessively high depending on the concentration of the solute. If this occurs, also shown in FIG. 2, it is possible to provide an area for flowing an auxiliary spray solution 18 around the metallic tube 3 and mix it with a solution sent from the LC in the neighborhood of the end of the metallic tube 3 so as to set the flow rate, viscosity, and electric conductivity to the conditions for continuing the electrospray stably.

Figure 3:
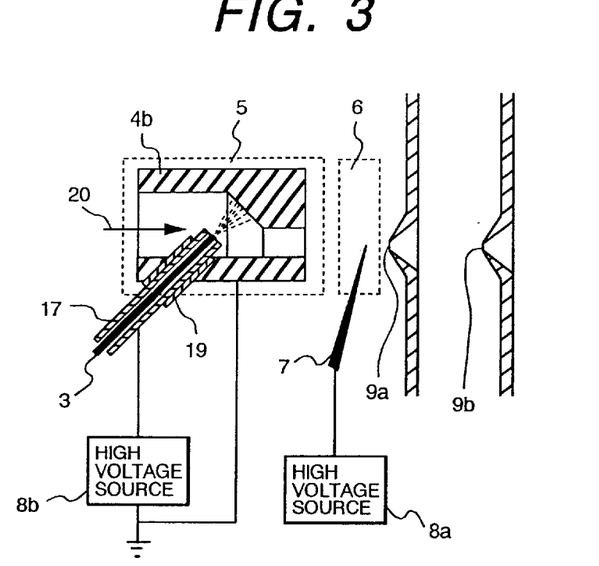
FIG. 3 is a schematic sectional view showing an embodiment in which the end of the metallic tube is placed in the volatilization portion and a sample solution is directly sprayed toward the metallic block.

As shown in FIG. 3, the end of the metallic tube 3 may be placed in the volatilization portion 6. Also as shown in FIG. 3, a solution may be sprayed directly toward the metallic block 4b. A sample solution is subjected to first ionization, that is, electrospray at a high voltage applied between the metallic tube 3 and the metallic block 4b by the high voltage source 8b. The metallic tube 3 and the metallic block 4b are insulated from each other by an insulating tube 19. Droplets sprayed to the metallic block 4b which is heated to a temperature higher than the boiling point of the solution are vaporized instantaneously and gaseous sample molecules are obtained. When sample molecules reach the corona discharge portion, they are chemically reacted with primary ions such as hydronium ions generated by corona discharge and ionization of sample molecules is realized by second ionization, that is, chemical ionization. Ions of sample molecules are fetched by the high vacuum portion 12 which is exhausted to about $10^{-3}$ Pa by the exhaust system 10b via the differential pumping portion 11 which is exhausted to from several tens Pa to several hundreds Pa by the ion introduction aperture 9a and the exhaust system 10a and the mass thereof is analyzed by the mass spectrometric portion 13.

To increase the arrival efficiency of sample molecules to the ionization portion, as shown in FIG. 3, it is possible to provide an inclined wall inside the metallic block 4b, electrostatically spray sample molecules toward the inclined wall in the oblique direction, and flow a gas 20 such as nitrogen gas toward the ionization portion. It is desirable to preheat the gas 20 at a temperature higher than the room temperature.

When large droplets are generated by electrospray in an apparatus having the constitution shown in FIG. 2, they cannot be vaporized perfectly in the vaporization portion 5 by the heated metallic block 4b and may reach the ionization portion 6 where a corona discharge is generated by the needle electrode 7 as they are. When droplets reach the portion where a corona is generated, there is a possibility that they short-circuit the needle electrode 7 and the ion introduction aperture 9a and the high voltage source 8a or others may be damaged.

Figure 4:
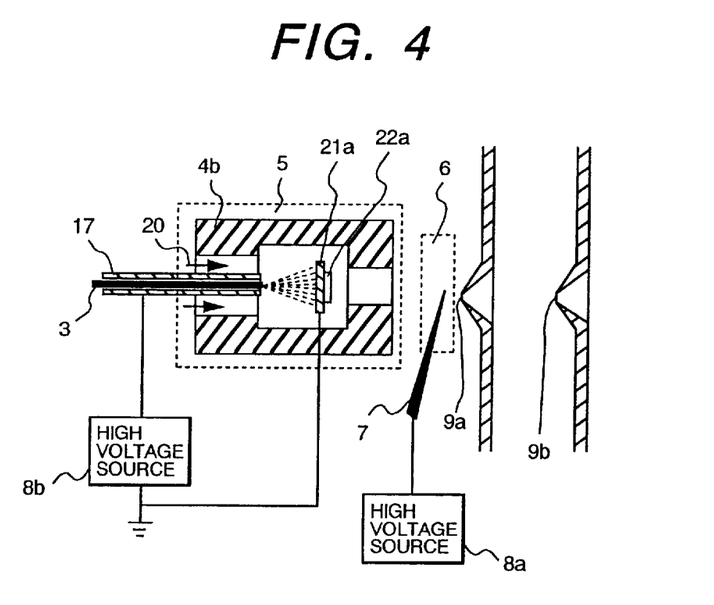
FIG. 4 is a schematic sectional view showing an embodiment in which a shielding plate for preventing large droplets from splashing and reaching the ionization portion is installed.

To prevent it, as shown in FIG. 4, it is possible to arrange an electrode 21a so as to shield the ionization portion 6 where a corona discharge is generated by the end of the metallic tube 3 and the needle electrode 7 and electrostatically spray droplets toward the electrode 21a. In this case, to increase the vaporization efficiency of droplets, it is desirable to heat the electrode 21a by a heater 22a beforehand. In an apparatus having the constitution shown in FIG. 4, gaseous molecules are transported and ionized in the ionization portion 6, so that a short-circuit due to droplets adhered to the needle electrode 7 can be avoided. In FIG. 4, the shape of the electrode 21a may be not only laminar but also meshed. To increase the arrival efficiency of sample molecules to the ionization portion 6, it is possible to flow a gas 20 toward the ionization portion 6 as shown in FIG. 3.

In the embodiments shown in FIGS. 2 to 4, a constitution in which a heated metallic block is used as a means for vaporizing droplets is shown. However, a method for irradiating infrared light may be used for vaporization of droplets.

Figure 5:
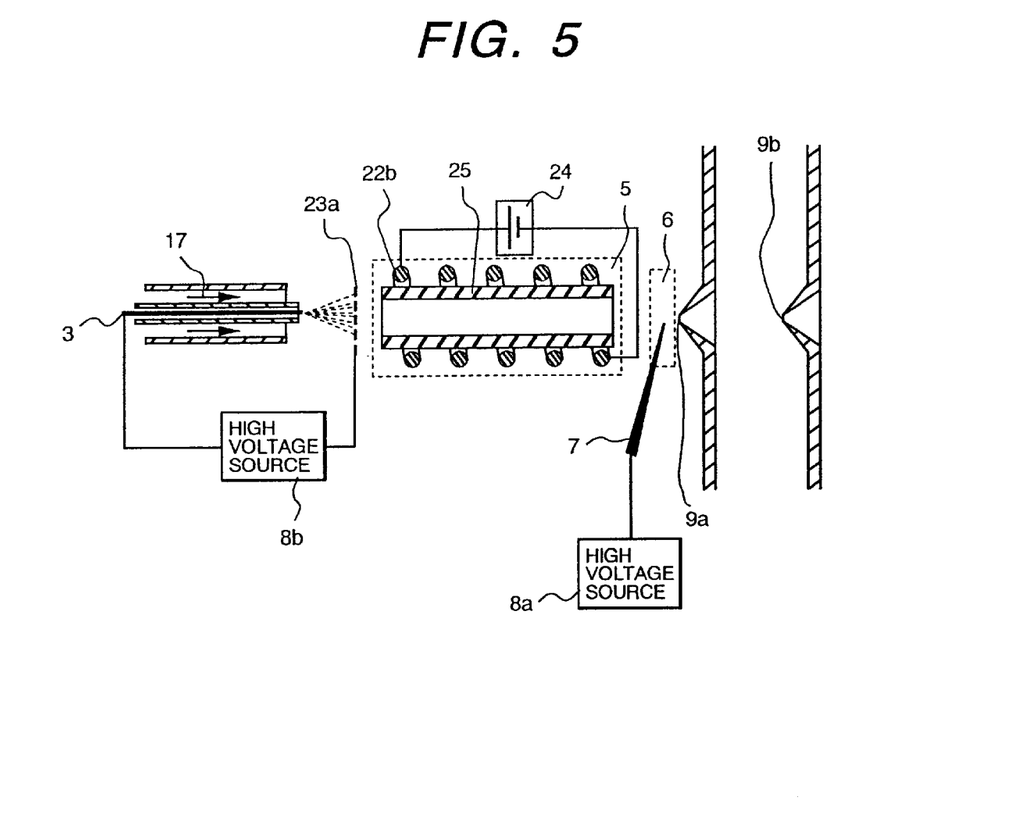
FIG. 5 is a schematic sectional view showing an embodiment in which irradiation of infrared light is used as a vaporization method of the vaporization portion.

FIG. 5 shows an embodiment using irradiation of infrared light as a vaporization means. A sample solution is electrostatically sprayed at a voltage applied between the metallic tube 3 and a mesh 23a. It is desirable that the mesh 23a is heated beforehand. Droplets obtained by spray are sent to the vaporization portion 5. infrared light emitted from a heater 22b connected to a power source 24 is irradiated to droplets in the vaporization portion 5 so as to vaporize them.

When the heater 22b is degraded because droplets collide directly with it, it is possible to install a glass tube 25 inside the heater 22b so as to protect it. To increase the vaporization efficiency of droplets, it is desirable to remove water vapor in the spray gas 17 beforehand. It is also desirable to heat the spray gas 17 at the room temperature or higher beforehand. Gaseous sample molecules obtained in the vaporization portion 5 are ionized in the ionization portion 6.

Figure 6:
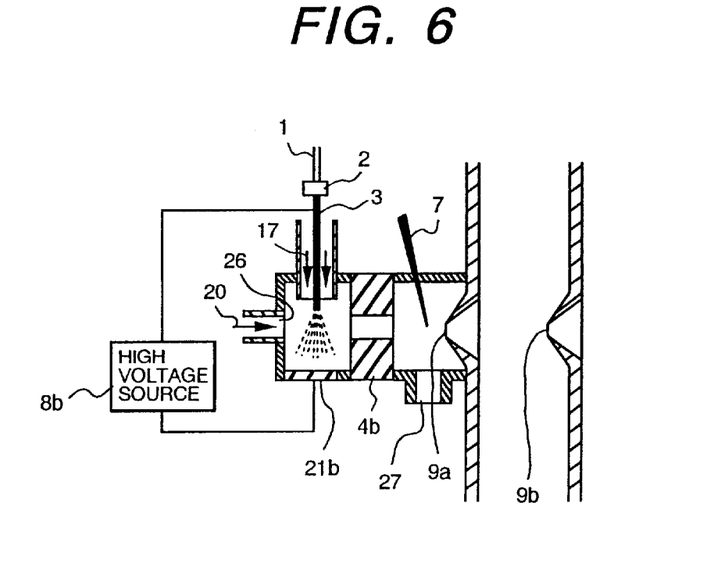
FIG. 6 is a schematic sectional view showing an embodiment in which a sample solution is sprayed perpendicularly to the center axis of the ion introduction aperture.

In an apparatus having the constitution shown in FIGS. 2 to 5, a sample solution containing nonvolatile compounds can be used in the LC/MS. However, when a sample solution containing nonvolatile compounds of an extremely high concentration is introduced into the ion source or the analysis requires more hours, it is possible to change the spray direction of the sample solution to a direction different from the arrangement direction of the ion introduction aperture. FIG. 6 shows an example in which a sample solution is sprayed perpendicularly to the center axis of the ion introduction aperture 9a. The sample solution introduced into the metallic tube 3 is sprayed toward an opposite electrode 21b. It is desirable that the electrode 21b is heated at a temperature higher than the boiling point of the solution beforehand.

Nonvolatile compounds are salted out on the electrode 21b. Volatile sample molecules are vaporized and introduced into the ionization portion 6 via the heated metallic block 4b. To increase the arrival efficiency of sample molecules to the ionization portion 6, it is possible to install a gas feed port 26 and flow a gas 20 such as dry nitrogen gas toward the ionization portion 6. It is desirable to heat the gas 20 beforehand. It is possible that by installing an exhaust port 27 and exhausting gas outside from the exhaust port, a gas flow is generated toward the ionization portion 6 from the portion where the solution is sprayed and sample molecules are introduced efficiently into the ionization portion 6.

In FIG. 6, the electrospray method is described as a method for spraying a solution. However, to change the spray direction of a sample solution to a direction different from the arrangement direction of the ion introduction aperture, it is possible to use a spray method other than electrospray, for example, heating spray or ultrasonic spray. When a substance to be analyzed is volatile, it is heated, vaporized, and diffused on the electrode 21b and reaches the ionization portion 6.

In an apparatus having the constitution shown in FIG. 6, nonvolatile compounds salt out on the electrode 21b. Therefore, by removing and cleaning only this electrode 21b, it can be maintained easily.

Figure 7:
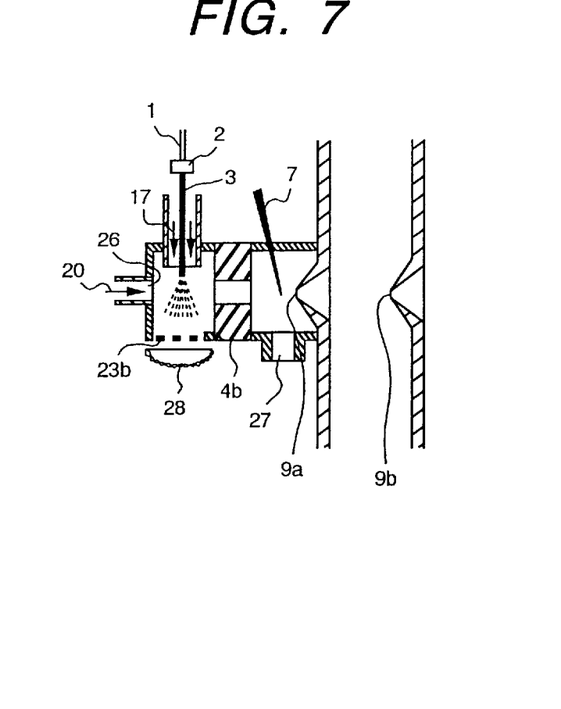
FIG. 7 is a schematic sectional view showing an embodiment in which a pan for collecting droplets is used.

FIG. 7 is a drawing showing a constitution in which a solution is sprayed toward a mesh 23b in place of the opposite electrode 21b shown in FIG. 6. It is desirable to heat the mesh 23b beforehand. A pan 28 can be installed behind the mesh 23b and maintained simply by exchanging. Furthermore, a solution collected in the pan 28 is sampled and an analytical means other than the mass spectrometry, for example, an analytical method using fluorescence or emission or an immunological analytical method may be executed for it.

Figure 8:
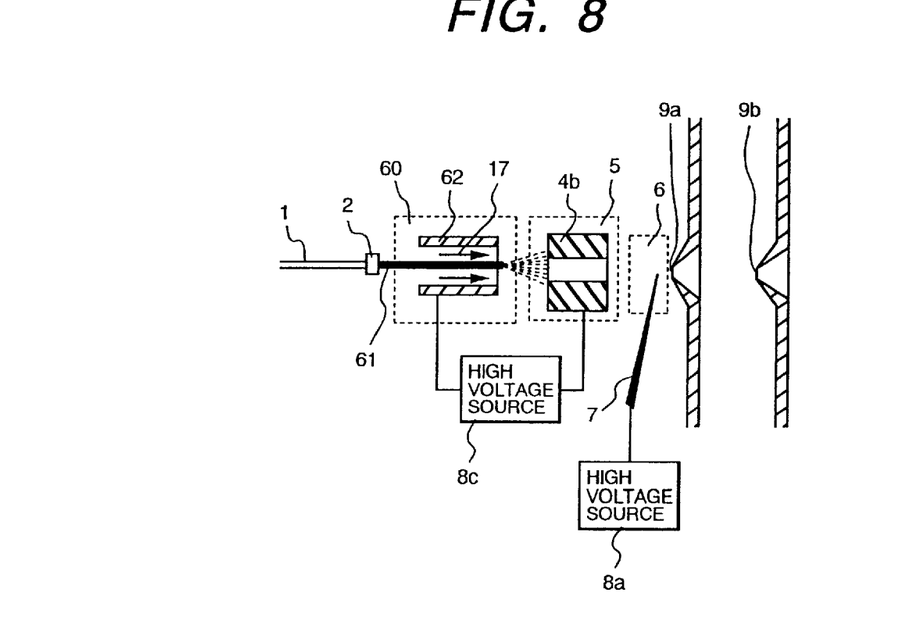
FIG. 8 is a schematic sectional view showing an embodiment in which a gas spray ionization method is used as a first ionization means.

The present invention is characterized in that nonvolatile compounds in a solution are ionized by the first ionization means and then removed by the electric field and a substance to be analyzed which is not ionized by the first ionization means is ionized by the second ionization means and analyzed. Therefore, if nonvolatile compounds can be ionized, the first ionization means may not be the electrospray method. FIG. 8 shows an embodiment in which the gas spray ionization method is used as a first ionization means.

A sample solution is introduced into a capillary 61 via the pipe 1 and the connector 2. The capillary 61 may be a metallic tube or an insulating tube. A spray gas introduction tube 62 is arranged around the capillary 61 and the spray gas 17 flows in it. When the spray gas 17 increases its speed, the solution is crushed to pieces and fine droplets are generated. In the droplets obtained by doing this, nonvolatile compounds which exist in the solution as ions are fetched. When the solvent is evaporated from the droplets, gaseous ions of the nonvolatile compounds are generated. The trajectory of the gaseous ions is curved by the potential applied to the needle electrode 7 installed in the ionization portion 6, so that the ions cannot reach the ion introduction aperture 9a. As a result, the nonvolatile compounds do not salt out in the neighborhood of the ion introduction aperture 9a and the ion introduction aperture 9a is not clogged up. A substance to be analyzed which is electrically neutral reaches the ionization portion 6 by diffusion in the same way as with the embodiment shown in FIG. 2 and is ionized and analyzed. To promote vaporization of droplets, the vaporization portion 5 comprising the heated metallic block 4b may be installed. Droplets are vaporized by heat while they are passing through the aperture of the metallic block 4b. To increase the efficiency for removing ions of nonvolatile compounds, it is possible to generate an electric field between the spray gas introduction tube 62 and the metallic block 4b by the high voltage source 8c. Ions of nonvolatile compounds are drifted by the electric field in the direction of the metallic block 4b or the spray gas introduction tube 62 according to the ion polarity and captured by the metallic block 4b or the spray gas introduction tube 62.

As shown by the above description, according to the present invention, even if a solution containing nonvolatile compounds of high concentration is introduced into the ion source, the capillary for spraying the solution and the aperture for fetching ions generated under the atmospheric pressure into a vacuum can be prevented from clogging up. As a result, a substance to be analyzed in the solution can be ionized stably for many hours and the ions can be introduced and analyzed in the spectrometric portion arranged in a vacuum. Therefore, a sample obtained from a living matter or environment can be analyzed without a complicated pretreatment being executed. Furthermore, a mobile phase containing a nonvolatile salt which cannot be used for many hours in a conventional LC/MS can be used, so that analysis b), the LC/MS fully utilizing the separation ability of the LC is possible.

Main symbols used in the drawings mentioned above are shown below in a batch.

1: Pipe, 2: Connector, 3: Metallic tube, 4a, 4b: Metallic blocks, 5: Vaporization portion, G: Ionization portion, 7: Needle electrode, 8a, 8b, 8c: High voltage sources, 9a, 9b: Ion introduction apertures: 10a, 10b: Exhaust systems, 11: Differential pumping portion, 12: High vacuum portion, 13: Mass spectrometric portion, 14: Liquid chromatograph, 15: Electrospray portion, 16: Splitter, 17: Spray gas, 18: Auxiliary spray solution, 19: Insulating tube, 20: Gas, 21a, 21b, 21c: Electrodes, 22a, 22b: Heaters, 23a, 23b: Meshes, 24: Power source, 25: Glass tube, 26: Gas feed port, 27: Exhaust port, 28: Pan, 30: Power source, 31: Deflection electrode, 32: Capture plate, 40: Spray gas outlet, 41: Shielding plate, 50: Mobile phase reservoir, 51: Pump, 52: Sample introduction portion, 53: Separation column, 60: Gas spray ion generation port, 61: Capillary, 62: Spray gas introduction tube.

What is claimed is:

1. A mass spectrometer comprising a sprayer for spraying a sample solution, a needle electrode for ionizing the sample contained in said sample solution, an aperture for introducing the ions of said sample into a lower pressure region having a pressure lower than a pressure of a region in which said needle electrode is disposed, and a mass spectrometric apparatus for analyzing the ions introduced from said aperture, wherein a direction of a spray caused by said sprayer is one of substantially perpendicular to and at an angle with respect to a center axis of said aperture, and a tip of said needle electrode is disposed facing an electrode having said aperture therein.

2. A mass spectrometer comprising a sprayer for spraying a sample solution by heating, a needle electrode for ionizing the sample contained in said sample solution, an aperture for introducing the ions of said sample into a lower pressure region having a pressure lower than a pressure of a region in which said needle electrode is disposed, and a mass spectrometric apparatus for analyzing the ions introduced from said aperture, wherein a direction of a spray caused by said sprayer is at an angle with respect to a center axis of said aperture, the direction of said spray is directed toward a wall surface, and a tip of said needle electrode is disposed facing an electrode having said aperture therein.

3. A mass spectrometer according to claim 2, wherein a vaporizer is disposed between said sprayer and said needle electrode.

4. A mass spectrometer according to claim 2, wherein said vaporizer includes means for heating and a metallic block.

5. A mass spectrometer comprising a sprayer for spraying a sample solution by heating, a needle electrode for ionizing the sample contained in said sample solution, an aperture for introducing the ions of said sample into a lower pressure region having a pressure lower than a pressure of a region in which said needle electrode is disposed, and a mass spectrometric apparatus for analyzing the ions introduced from said aperture, wherein a direction of a jet stream caused by said sprayer is at an angle with respect to a center axis of said aperture, and a tip of said needle electrode is disposed facing an electrode having said aperture therein.

* * * * *